United States Patent
Brain

Patent Number: 5,297,547
Date of Patent: Mar. 29, 1994

[54] LARYNGEAL MASK CONSTRUCTION

[76] Inventor: Archibald I. J. Brain, Sandford House, Sancourt Gardens, Longcross Road, Chertsey, Surrey KT16 0DJ, United Kingdom

[21] Appl. No.: 922,132

[22] Filed: Jul. 30, 1992

[51] Int. Cl.$^5$ .............................................. A61M 16/00
[52] U.S. Cl. ............................ 128/207.15; 128/207.14
[58] Field of Search ....................... 128/200.26, 207.14, 128/207.15

[56] References Cited

U.S. PATENT DOCUMENTS

| | | | |
|---|---|---|---|
| 4,509,514 | 4/1985 | Brain | 128/207.15 |
| 4,995,388 | 2/1991 | Brain | 128/207.15 |

Primary Examiner—Edgar S. Burr
Assistant Examiner—Aaron J. Lewis
Attorney, Agent, or Firm—Hopgood, Calimafde, Kalil, Blaustein & Judlowe

[57] ABSTRACT

A laryngeal mask has an inflatable ring configured, upon inflation, to establish a peripheral seal around a patient's laryngeal inlet. Installation (insertion) is made in the fully deflated state, wherein the structural relation between the body of the mask and the inflatable ring is such that deflated ring surfaces become tightly opposed to each other so as to form a thin flange which peripherally surrounds the body of the mask and is concave on the posterior side of the mask; the concave flange effectively displaces all ring material away from the aperture of the mask, in the manner of the upturned brim of a hat. The concave flange is softly yieldable in its confinement by local body structures encountered in the course of mask insertion. And it is an important feature that the distal end of the deflated ring is adapted not only to smoothly ride posterior contours of the throat and pharynx but also to gently cam the epiglottis out of the path of insertial displacement of the mask while also assuring that the distal end of the deflated mask smoothly enters the upper sphinctral region of the oesophagus. Once thus insertionally located, ring inflation will assuredly establish the desired peripheral seal of the mask around the laryngeal inlet.

9 Claims, 2 Drawing Sheets

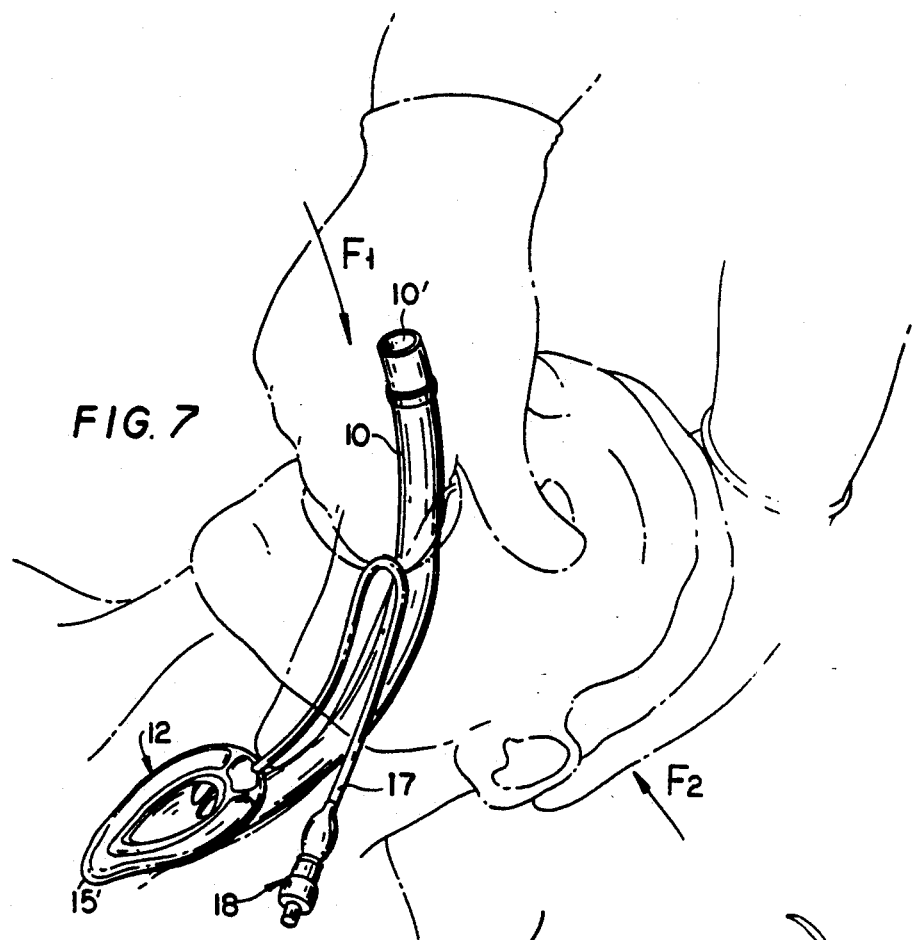
FIG. 7
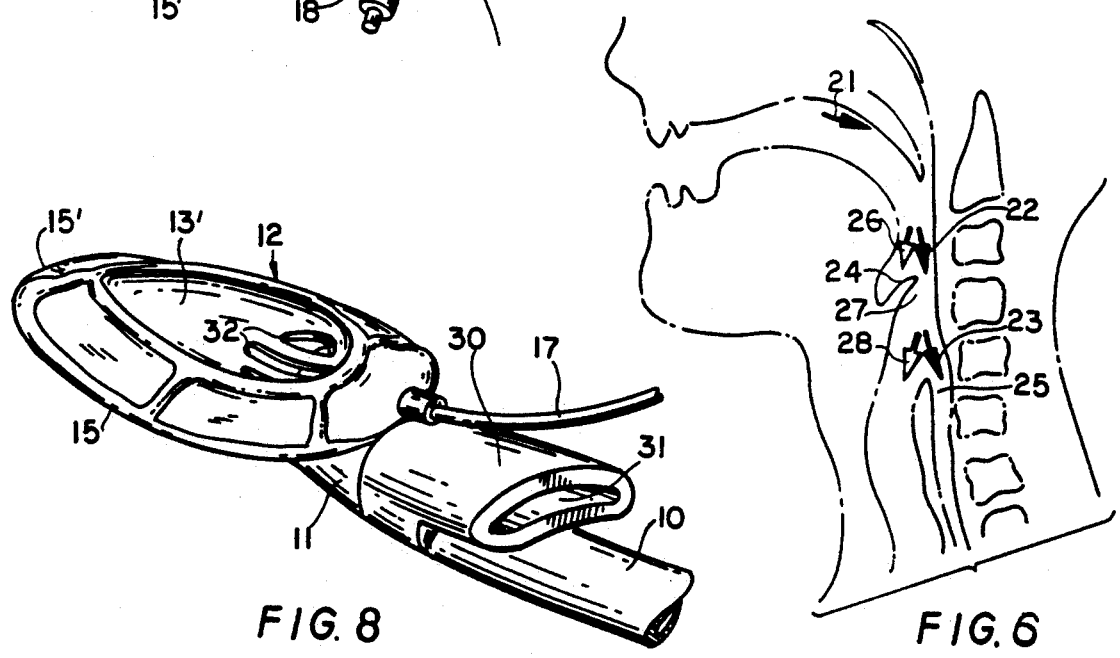
FIG. 8
FIG. 6

LARYNGEAL MASK CONSTRUCTION

BACKGROUND OF THE INVENTION

The invention relates to laryngeal masks, illustratively of varieties disclosed in U.S. Pat. Nos. 4,509,514 and 4,995,388, and in U.K. Patent No. 2,205,499. Such masks are artificial airway devices to facilitate lung ventilation in an unconscious patient. More specifically, the invention pertains to such a device designed for placement in the pharynx of the patient in order to prevent airway obstruction and to permit either spontaneous or controlled ventilation.

U.K. Patent No. 2,205,499 describes a flexible web closing the rear of the lumen of the mask and providing a pocket having a transverse slit opening toward the aperture of the airway tube, for receiving the end of a substantially rigid introducing tool. This pocket is effective when used with the introducing tool; however, it may act as a dirt-trap since secretions or blood may lodge in the pocket and thereby escape sterilization. The introducing tool may be required to elevate the epiglottis after inserting the mask, since insertion may push the epiglottis into a down-folded position, causing partial airway obstruction.

BRIEF STATEMENT OF THE INVENTION

It is an object of the invention to provide laryngeal-mask construction which features ease and enhance reliability of correct insertion.

It is a specific object to meet the above object with a construction which does not require the use of an insertion tool and which avoids provision of a pocket or other potential dirt trap in the lumen of the mask, thus avoiding the danger of transmitting an infection from one patient to another.

The invention achieves these objects in a construction wherein the mask has an inflatable ring configured to establish a peripheral seal around the laryngeal inlet and wherein insertion must be made in the fully deflated state. In the fully deflated state, the structural relation between the body of the mask and the inflatable ring is such that deflated ring surfaces become tightly opposed to each other so as to form a thin flange which peripherally surrounds the body of the mask and is concave on the posterior side of the mask; the concave flange effectively displaces all ring material away from the aperture of the mask, in the manner of the upturned brim of a hat. The concave flange is softly yieldable in its confinement by local body structures encountered in the course of mask insertion. And it is an important feature that the distal end of the deflated ring is adapted not only to smoothly ride posterior contours of the throat and pharynx but also to gently cam the epiglottis out of the path of insertial displacement of the mask while also assuring that the distal end of the deflated mask smoothly enters the upper sphinctral region of the oesophagus. Once thus insertionally located, ring inflation will assuredly establish the desired peripheral seal of the mask around the laryngeal inlet.

DETAILED DESCRIPTION

The invention will be described in detail for a preferred embodiment, in conjunction with the accompanying drawings, in which:

FIG. 6 is a simplified fragmentary view in side elevation to show desired directions of orientation of the distal end of the mask of FIGS. 1 and 2, in the course of insertion in a patient;

FIG. 7 is a simplified perspective view of the mask of FIGS. 1 and 2 in fully deflated state, in the context of the process of insertion via the mouth, throat and pharynx of a patient; and FIG. 8 is a view in three-quarter perspective, showing the anterior side of fully deflated laryngeal-mask structure incorporating an additional feature of the invention.

Figure 1:
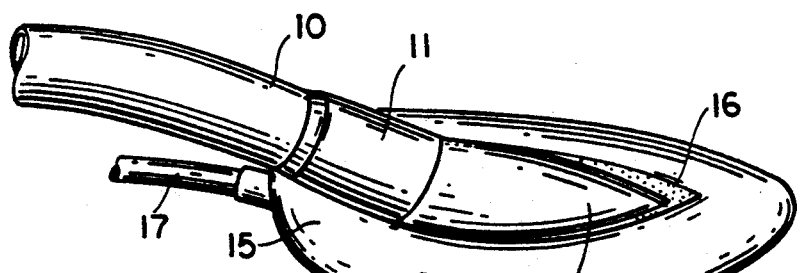
FIG. 1 is a perspective view of an inflatable laryngeal mask of the invention, in inflated condition, as viewed from a three-quarter aspect involving the posterior side of the mask.
Figure 2:
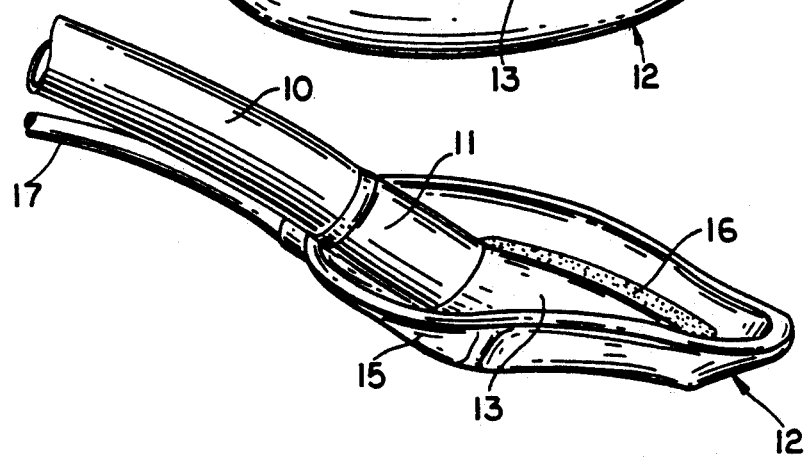
FIG. 2 is a view similar to the view of FIG. 1, but showing the mask in fully deflated condition.
Figure 3:
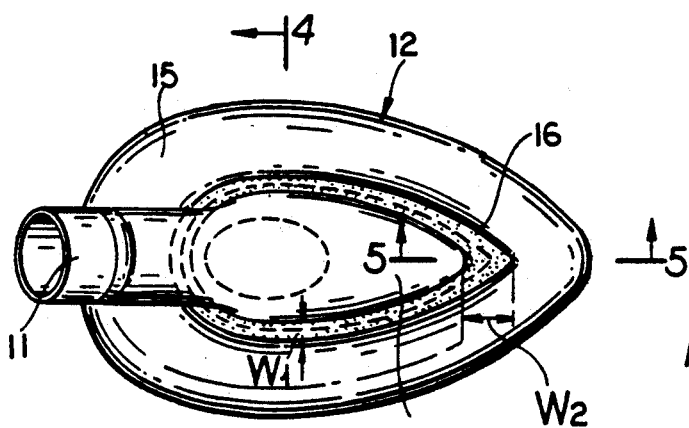
FIG. 3 is a plan view of the posterior side of the mask of FIGS. 1 and 2, in inflated state.
Figure 4:
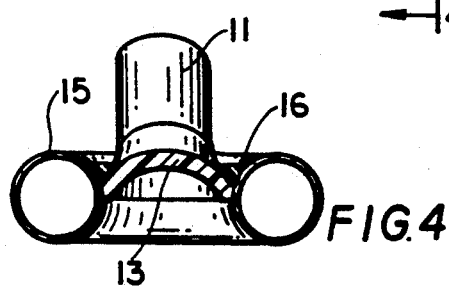
FIG. 4 is an enlarged sectional view taken at the plane 4—4 of FIG. 3.
Figure 4A:
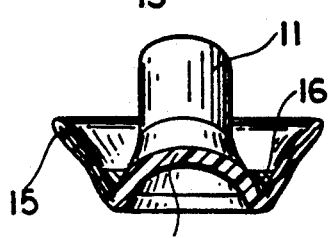
FIG. 4A is an enlarged sectional view taken at the plane 4—4 of FIG. 3 but for the fully deflated condition of the mask.

Referring to FIGS. 1 to 5, the invention is seen in application to a laryngeal mask comprising an elongate airway tube 10, fitted at its inner end to the inlet-port formation 11 of an inflatable mask 12. The inlet formation 11 is part of the body 13 of the mask. The mask body 13 is elongate and generally elliptical and is seen in FIG. 3 to have a tear-drop shape wherein the distal end is distally more pointed while the proximal end is more proximally rounded. The body 13 is seen in FIGS. 4 and 4A to be convex on its posterior side and concave on its anterior side, thus defining a bowl shape which is to face the laryngeal inlet and which is characterized by a peripheral rim of tear-drop shape and in essentially a single geometric plane. The radial inner limit of an inflatable ring 15 is circumferentially continuously connected to the rim of the bowl shaped body 13, defining a V-shaped groove which peripherally surrounds the posterior side of the mask, at juncture of ring 15 with body 13, as best seen in FIG. 4.

In accordance with a feature of the invention, this posteriorly exposed V-groove is filled with a flexible material such as silicone-rubber glue, and in the drawings this filling is designated 16. Inflation and deflation of ring 15 is by way of an elongate flexible tube 17 which is seen in FIG. 7 to be terminated by a two-way check valve 18 which is able to selectively hold a given inflation pressure or a given reduced pressure to achieve full deflation of ring 15; in this connection, a suitable commercially available check-valve product is the Bespak BK333 medical check valve.

Figure 5:
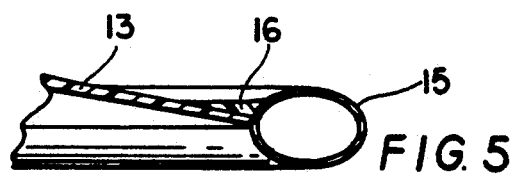
FIG. 5 is an enlarged fragmentary sectional view taken at the plane 5—5 of FIG. 3.
Figure 5A:
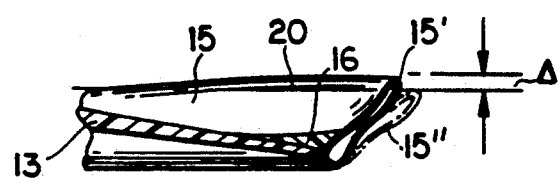
FIG. 5A is an enlarged sectional view taken at the plane 5—5 of FIG. 3 but for the fully deflated condition of the mask.

Also in accordance with a feature of the invention, the filling 16 which preferentially and resiliently unites body-rim material to adjacent posterior material of ring 15 is of substantially uniform radial width $W_1$ for most of the peripheral extent of the body-to-ring juncture, except that as seen in FIGS. 3, 5 and 5A, the width $W_2$ of filling 16 is greater at the distal end. In addition, the thickness of body 13 material gradually reduces in the distal direction, whereby to enhance the resilience of the distal end of the body.

The net result of these factors is to predictably form an acutely angled distal end 15' of the flange which results from full deflation of ring 15. In FIG. 5A, this angled distal end 15' is seen to project distally for piloting contact with posterior structures of the patient's mouth, throat and pharynx, with the feature of affording a range Δ of resiliently loaded contact with these posterior features throughout the course of mask insertion. FIG. 5A, the phantom outline 15" will be understood to indicate the deflected condition of the distal end 15', by reason of resiliently loaded piloting contact with a local posterior contour 20 of the patient's throat. FIGS. 6 and 7 are useful in explaining how such resiliently loaded piloting contact is maintained all the way to the installed location wherein the flexible distal end 15' of the deflated ring 15 safely enters the upper sphinctral region of the oesophagus. Thus located, ring 15 is inflated to establish its circumferential seal around the laryngeal inlet, thereby assuring airway-tube communication solely with the laryngeal inlet.

FIG. 6 is a schematic diagram to show by means of solid arrows 21, 22, 23 the course of deflated-mask displacement in a given installation, it being noted that the flexible distal end 15' of the mask pilots on all posterior contours of the patient's throat and pharynx, safely past the epiglottis 24 and with entry into the upper sphinctral region 25. In thus passing the epiglottis, the distal end 15' will be understood to present an acutely angled flange surface having cam engagement with the epiglottis whereby to deflect the tip end of the epiglottis in the counterclock wise direction (in the sense of FIG. 7), thereby avoiding any tendency to downwardly displace or double-back the epiglottis. Were it not for the described acutely angled and resiliently loaded distal end 15' of the deflated ring 15, opportunity would be presented for fouling encounter with the epiglottis (suggested by an outlined arrow 26) and/or for distal-end entry into the laryngeal inlet 27 (suggested by an outlined arrow 28).

FIG. 7 is a simplified diagram to show the manner in which it is recommended that a physician or technician can quickly, safely and efficiently install the described mask 12 with its airway tube 10 and inflation/deflation means 17. With one hand slightly elevating and supporting the patient's head, the deflated mask is inserted through the mouth while using the index finger with the other hand to engage tube 10 at juncture 11 with the mask, it being noted that the flexible piloting distal end 15' is thrust, by index-finger action on mask 12, into the course of piloting contact described in connection with FIG. 6; heavy arrows $F_1, F_2$ will be understood to suggest opposing forces applied by the operator in the course of mask insertion, with the further understanding that the index finger continuously applies its thrusting pressure on mask 12. Once sufficiently inserted to the point of sensed engagement of distal end 15' with the inlet to the upper sphinctral region, the index finger is removed, ring 15 is inflated (to establish a peripheral seal around the laryngeal inlet), and lung-ventilating or the like connections are made to the airway inlet 10'. Of course, gloves should be worn throughout the insertional process.

In the described insertional process, an experienced operator will have no trouble keeping his index finger in properly thrusting application to mask 12, but a less skillful operator may accidentally allow his index finger to slip out of this thrusting engagement. To reduce the chance of such an accident, FIG. 8 shows a slight modification wherein a finger-locating fixture 30, secured either to airway tube 10 or to the inlet-port formation 11 of the mask body, provides a pocket opening 31 for such index-finger location.

FIG. 8 also serves to indicate preference that the bowl of mask body 13 be lined with a thin layer 131 of flexible material such as silicone rubber, having plural slit openings 32, in register with the airway-inlet port, so that, even in the case of a less-than-perfect installation of the mask, the epiglottis will be unable to impair the integrity of a sealed ventilating passage from tube 10 to the laryngeal inlet.

What is claimed is:

1. As an article of manufacture, an artificial airway device to facilitate a patient's lung ventilation, comprising an airway tube and a laryngeal mask at one end of said tube, said mask comprising an elongate generally elliptical body having between distal and proximal ends thereof a concave anterior side and a convex posterior side, said body having a rim of generally tear-drop shape wherein the distal end is more pointed distally and the proximal end is more rounded proximally, an inflatable ring of material that is more flexible than the material of said body, said ring having a radially inner limit that is peripherally continuously connected to and surrounds said body rim and that is configured upon inflation to form a seal of said mask around the circumference of the laryngeal inlet, the posterior side of said body having an airway-port connection which is open to the concave anterior side and on a directional alignment which is generally directed toward the larynx via the laryngeal inlet when said ring is inflated and sealed around the laryngeal inlet, the posterior side of said body having peripherally continuous juncture of generally V-shaped section at adjacency with the material of said ring, said V-shaped section being defined by and between (a) by a peripherally continuous annular wall-surface portion of said ring and (b) a peripherally continuous annular wall-surface portion of the posterior side of said body, and a peripherally continuous filler of flexible material contained within and adhered to the adjacent wall-surface portions of said generally V-shaped section, whereby body stiffness preferentially extends over adjacent posterior material of said ring, so that upon deflation of said ring, the material of said ring forms a resilient concave annular flange peripherally continuously surrounding the posterior side of said body, the distal end of said flange being configured for resiliently loaded sliding contact with posterior contours of the patient's mouth and throat in the course of mask insertion into ring placement for inflation to establish said seal around the laryngeal inlet.

2. As an article of manufacture, a laryngeal mask adapted for connection to one end of an airway tube to thereby constituted an artificial airway for ventilation of a patient's lung, said mask comprising an elongate generally elliptical body having between distal and proximal ends a concave anterior side and a convex posterior side, said body having a rim of generally tear-drop shape wherein the distal end is more pointed distally and the proximal end is more rounded proximally, an inflatable ring of material that is more flexible than the material of said body said ring having a radially inner limit that is peripherally continuously connected to and surrounds said body rim and that is configured upon inflation to form a seal of said mask around the circumference of the laryngeal inlet, the posterior side of said body having an airway-port connection which is open to the concave anterior side and on a directional alignment which is generally generally directed to the larynx via the laryngeal inlet when said ring is inflated and sealed around the laryngeal inlet, the posterior side of said body having peripherally continuous juncture of generally V-shaped section at adjacency with the material of said ring, said V-shaped section being defined by a peripherally continuous annular wall-surface portion of said ring and by a peripherally continuous annular wall-surface potion of the posterior side of said body, and a peripherally continuous filler of flexible material contained within and adhered to the adjacent wall-surface portions of said generally V-shaped section, whereby body stiffness preferentially extends over posterior material of said ring, so that upon deflation of said ring, the material of said ring forms a resilient concave annular flange peripherally continuously surrounding the posterior side of said body, the distal end of said flange being configured for resiliently loaded sliding contact with posterior contours of the patient's mouth and throat in the course of mask insertion into ring placement for inflation to establish said seal around the laryngeal inlet.

3. The article of claim 1 or claim 2, in which the material of said body and the material of said ring are both silicone rubber, and the material of said filler is a silicone glue.

4. The article of claim 1 or claim 2, in which the material of said body is a silicone rubber and the material of said ring is a silicone rubber, the thickness of ring material being less than that of body material, whereby to establish the relative flexibility of said ring and stiffness of said body.

5. The article of claim 1 or claim 2, in which the material of said body is a silicone rubber and the material of said ring is a silicone rubber, the thickness of ring material being less than that of body material, the thickness of body material being less at the distal end than at the proximal end of said body, whereby to enhance the flexibility of the distal end of said body.

6. The article of claim 1 or claim 2, in which the filled extent of said generally V-shaped section is greatest at the distal end of said mask, whereby to enhance the resilient load of said sliding contact and to reduce susceptibility of the distal end of said annular flange to locally and transiently shift from concave to convex relation with the posterior side of said mask.

7. The article of claim 1 or claim 2, in which the concave surface of the body of said mask is lined with a relatively thin flexible member having a plurality of spaced apertures in general register with said alignment of said airway-port connection with the axis of the laryngeal inlet.

8. As an article of manufacture, an artificial airway device to facilitate a patient's lung ventilation, comprising an airway tube and a laryngeal mask at one end of said tube, said mask comprising an elongate generally elliptical body having between distal and proximal ends thereof a concave anterior side and a convex posterior side, said body having a rim of generally tear-drop shape wherein the distal end is more pointed distally and the proximal end is more rounded proximally, an inflatable ring of material that is more flexible than the material of said body, said ring having a radially inner limit that is peripherally continuously connected to and surrounds said body rim and that is configured upon inflation to form a seal of said mask around the circumference of the laryngeal inlet, the posterior side of said body having an airway-port connection which is open to the concave anterior side and on a directional alignment which is generally directed toward the larynx via the laryngeal inlet when said ring is inflated and sealed around the laryngeal inlet, and a finger-locating pocket is fixedly related to said airway tube at or near juncture with the body of said mask.

9. As an article of manufacture, an artificial airway device to facilitate a patient's lung ventilation, comprising an airway tube and a laryngeal mask at one end of said tube, said mask comprising an elongate generally elliptical body having between distal and proximal ends thereof a concave anterior side and a convex posterior side, said body having a rim of generally tear-drop shape wherein the distal end is more pointed distally and the proximal end is more rounded proximally, an inflatable ring of material that is more flexible than the material of said body, said ring having a radially inner limit that is peripherally continuously connected to and surrounds said body rim and that is configured upon inflation to form a seal of said mask around the circumference of the laryngeal inlet, the posterior side of said body having an airway-port connection which is open to the concave anterior side and on a directional alignment which is generally directed toward the larynx via the laryngeal inlet when said ring is inflated and sealed around the laryngeal inlet, and a finger-locating pocket is fixedly related to the body of said mask at or near juncture with said airway tube.

* * * * *